US012692265B2

(12) United States Patent
Muthusamy et al.

(10) Patent No.: US 12,692,265 B2
(45) Date of Patent: Jul. 28, 2026

(54) SOLID STATE FORMS OF ENSIFENTRINE AND PROCESS FOR PREPARATION THEREOF

(71) Applicant: ASSIA CHEMICAL INDUSTRIES LTD., Tel Aviv (IL)

(72) Inventors: Anantha Rajmohan Muthusamy, Sivakasi (IN); Rahul Kumar Reddy Putikum, Mahabubnagar (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 269 days.

(21) Appl. No.: 18/695,401

(22) PCT Filed: Oct. 25, 2022

(86) PCT No.: PCT/US2022/047642
§ 371 (c)(1),
(2) Date: Mar. 26, 2024

(87) PCT Pub. No.: WO2023/076205
PCT Pub. Date: May 4, 2023

(65) Prior Publication Data

US 2024/0391916 A1 Nov. 28, 2024

(30) Foreign Application Priority Data

| | | | |
|---|---|---|---|
| Oct. 29, 2021 | (IN) | ............................. | 202111049528 |
| Nov. 24, 2021 | (IN) | ............................. | 202111054255 |
| Dec. 24, 2021 | (IN) | ............................. | 202111060734 |

(51) Int. Cl.
*C07D 471/04* (2006.01)
*A61K 31/519* (2006.01)

(52) U.S. Cl.
CPC .......... *C07D 471/04* (2013.01); *A61K 31/519* (2013.01)

(58) Field of Classification Search
None
See application file for complete search history.

(56) References Cited

U.S. PATENT DOCUMENTS

| | | | |
|---|---|---|---|
| 6,794,391 | B2 | 9/2004 | Oxford et al. |
| 9,062,047 | B2 | 6/2015 | Walker et al. |
| 10,463,665 | B2 † | 11/2019 | Spargo |

OTHER PUBLICATIONS

Stephen Byrn, et al., “Pharmaceutical Solids: A Strategic Approach to Regulatory Considerations”, Pharmaceutical Research, vol. 12, No. 7, Jul. 1, 1995 (Jul. 1, 1995), pp. 945-954.
International Search Report and Written Opinion of the International Searching Authority issued in corresponding application PCT/US2022/047642 mailed Jan. 27, 2023 (15 pages).

† cited by third party

*Primary Examiner* — Leslie A. Royds Draper
(74) *Attorney, Agent, or Firm* — Carter, DeLuca & Farrell LLP

(57) ABSTRACT

The present disclosure encompasses solid state forms of Ensifentrine, in embodiments crystalline polymorphs or salts of Ensifentrine, particularly Ensifentrine ethane-1.2-disulfonate, processes for preparation thereof, and pharmaceutical compositions thereof.

12 Claims, 7 Drawing Sheets

Figure 1: X-ray powder diffraction pattern (XRPD) of Ensifentrine ethane-1,2-disulfonate Form ES1
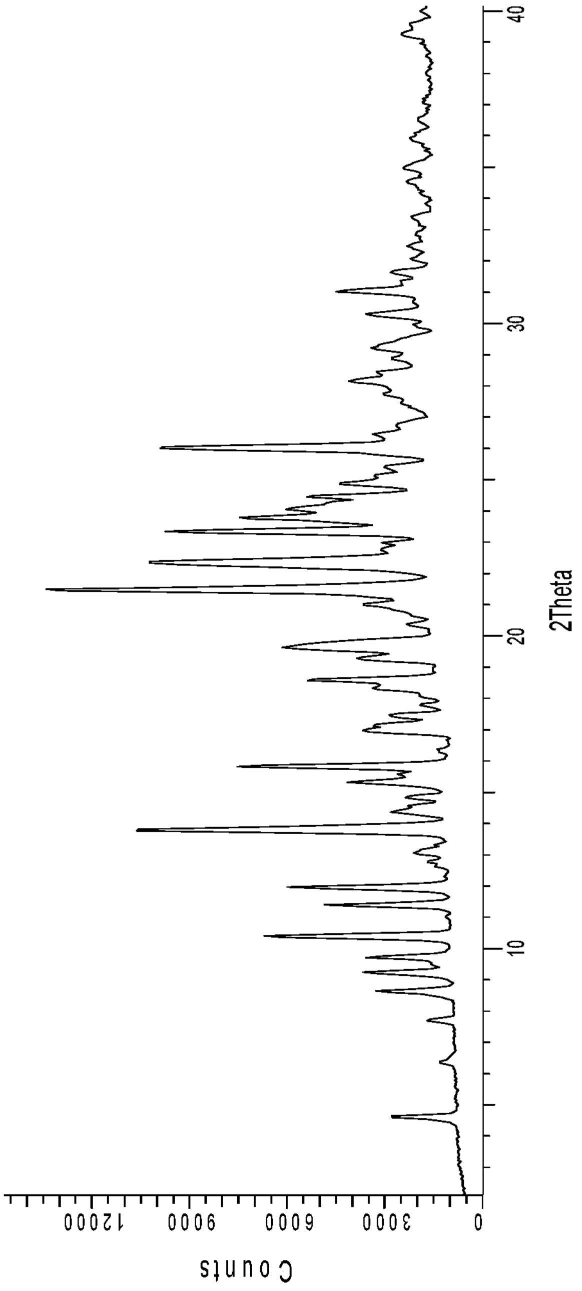

Figure 2: X-ray powder diffraction pattern (XRPD) of Ensifentrine ethane-1,2-disulfonate Form ES2
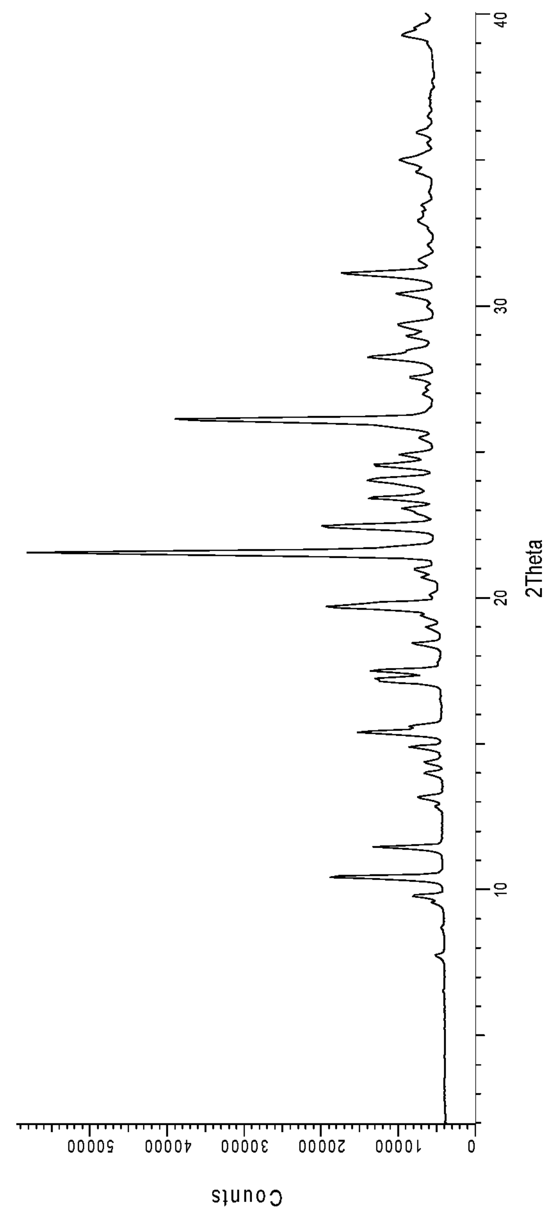

Figure 3: X-ray powder diffraction pattern (XRPD) of Ensifentrine ethane-1,2-disulfonate Form ES3
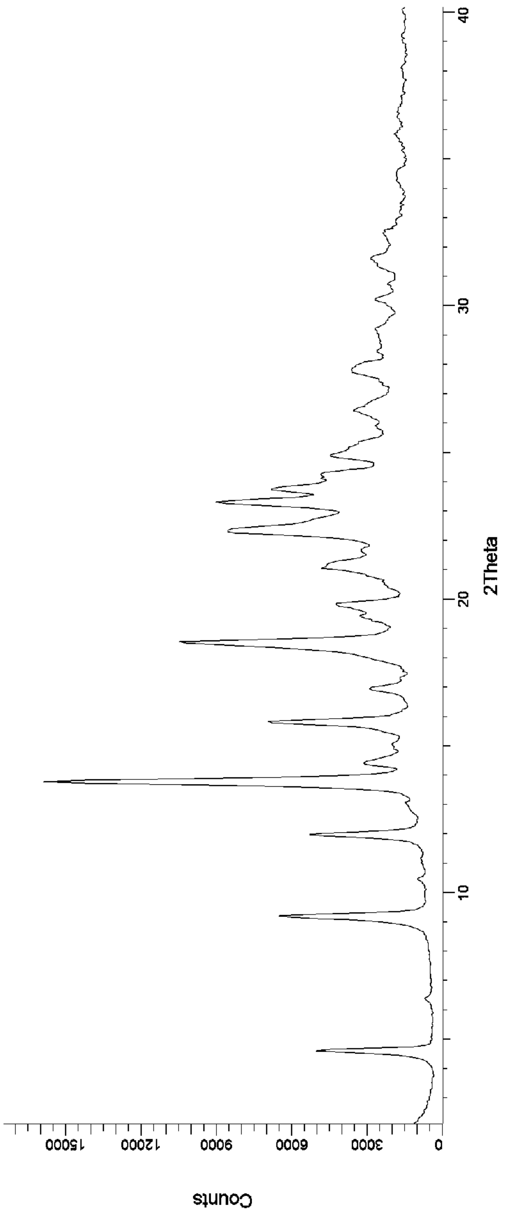

Figure 4: X-ray powder diffraction pattern (XRPD) of amorphous Ensifentrine ethane-1,2-disulfonate
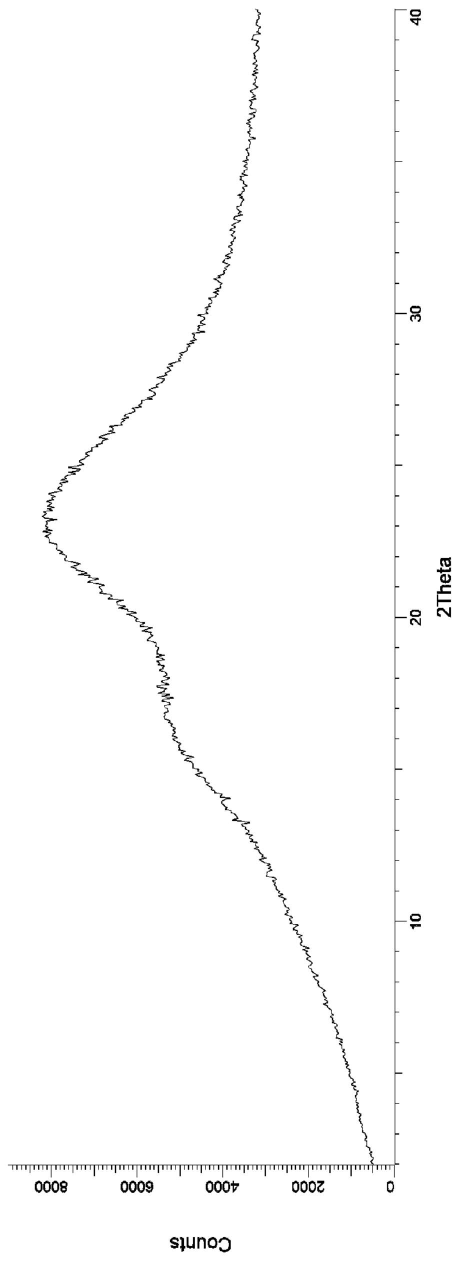

$^{13}C$ Solid State NMR Spectrum of Form ES2 of Ensifentrine Ethane-1,2-Disulfonate (at the range of 0-100 ppm)

13C Solid State NMR Spectrum of Form ES2 of Ensifentrine Ethane-1,2-Disulfonate (at the range of 100-200 ppm)

106.334
112.792
114.726
130.848
131.621
132.812
135.378
136.962
140.012
146.911
149.038
151.991
154.307
157.179
161.287 ppm

SOLID STATE FORMS OF ENSIFENTRINE AND PROCESS FOR PREPARATION THEREOF

CROSS REFERENCE TO RELATED APPLICATIONS

This application is a National Stage of, and claims priority to and the benefit of, International Patent Application No. PCT/US2022/047642, filed on Oct. 25, 2022, which, in turn, claims the benefit of and priority to, Indian Provisional Application No. 202111049528, filed on Oct. 29, 2021; Indian Provisional Application No. 202111054255, filed on Nov. 24, 2021 and Indian Provisional Application No. 202111060734, filed on Dec. 24, 2021, the entire disclosures of each of which are incorporated by reference herein.

FIELD OF THE DISCLOSURE

The present disclosure encompasses solid state forms of Ensifentrine, in embodiments crystalline polymorphs or salts of Ensifentrine, particularly Ensifentrine ethane-1,2-disulfonate, processes for preparation thereof, and pharmaceutical compositions thereof.

BACKGROUND OF THE DISCLOSURE

Ensifentrine, 9,10-dimethoxy-2-(2,4,6-trimethylphenylimino)-3-(N-carbamoyl-2-aminoethyl)-3,4,6,7-tetrahydro-2H-pyrimido(6,1-a) isoquinolin-4-one, has the following chemical structure:

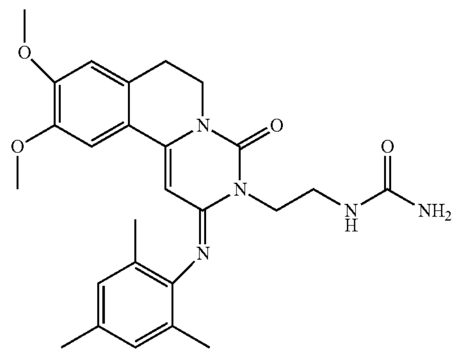 [SMILES: COc1cc2c(cc1OC)-c1c/c(=N\c3c(C)cc(C)cc3C)n(CCNC(N)=O)c(=O)n1CC2]

Ensifentrine is a first-in-class, inhaled, dual inhibitor of the phosphodiesterase 3 (PDE3) and phosphodiesterase 4 (PDE4) enzymes, and it is developed for the treatment of chronic obstructive pulmonary disease (COPD), cystic fibrosis and asthma.

The compound is described in U.S. Pat. No. 6,794,391. Crystalline form of Ensifentrine is described in U.S. Pat. No. 9,062,047. Ensifentrine ethane-1,2-disulfonate and other salts of Ensifentrine are described in U.S. Pat. No. 10,463,665.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Ensifentrine.

SUMMARY OF THE DISCLOSURE

The present disclosure provides crystalline polymorphs or salts of Ensifentrine, particularly Ensifentrine ethane-1,2-disulfonate, processes for preparation thereof, and pharmaceutical compositions thereof. In embodiments, the present disclosure provides crystalline forms of Ensifentrine ethane-1,2-disulfonate designated as Form ES1, ES2 and Form ES3 (defined herein). These crystalline polymorphs can be used to prepare other solid state forms of Ensifentrine, Ensifentrine salts, particularly Ensifentrine ethane-1,2-disulfonate and their solid state forms.

The present disclosure also provides uses of the said solid state forms of Ensifentrine and salts thereof, particularly Ensifentrine ethane-1,2-disulfonate in the preparation of other solid state forms of Ensifentrine or salts, particularly Ensifentrine ethane-1,2-disulfonate thereof.

The present disclosure provides crystalline polymorphs of Ensifentrine and salts of Ensifentrine, particularly Ensifentrine ethane-1,2-disulfonate for use in medicine, including for the treatment of Chronic obstructive pulmonary disease (COPD), cystic fibrosis and asthma.

The present disclosure also encompasses the use of crystalline polymorphs of Ensifentrine and salts of Ensifentrine, particularly Ensifentrine ethane-1,2-disulfonate of the present disclosure for the preparation of pharmaceutical compositions and/or formulations.

In another aspect, the present disclosure provides pharmaceutical compositions comprising crystalline polymorphs of Ensifentrine and salts of Ensifentrine, particularly Ensifentrine ethane-1,2-disulfonate according to the present disclosure.

The present disclosure includes processes for preparing the above mentioned pharmaceutical compositions. The processes includes combining any one or a combination of the crystalline polymorphs of Ensifentrine and salts of Ensifentrine, particularly Ensifentrine ethane-1,2-disulfonate with at least one pharmaceutically acceptable excipient.

The crystalline polymorph of Ensifentrine and salts of Ensifentrine, particularly Ensifentrine ethane-1,2-disulfonate as defined herein and the pharmaceutical compositions or formulations of the crystalline polymorph of Ensifentrine and salts of Ensifentrine, particularly Ensifentrine ethane-1,2-disulfonate may be used as medicaments, such as for the treatment of Chronic obstructive pulmonary disease (COPD), cystic fibrosis and asthma.

The present disclosure also provides methods of treating Chronic obstructive pulmonary disease (COPD), cystic fibrosis and asthma, by administering a therapeutically effective amount of any one or a combination of the crystalline polymorphs of Ensifentrine and salts of Ensifentrine, particularly Ensifentrine ethane-1,2-disulfonate of the present disclosure, or at least one of the above pharmaceutical compositions, to a subject suffering from Chronic obstructive pulmonary disease (COPD), cystic fibrosis and asthma, or otherwise in need of the treatment.

The present disclosure also provides uses of crystalline polymorphs of Ensifentrine and salts of Ensifentrine, particularly Ensifentrine ethane-1,2-disulfonate of the present disclosure, or at least one of the above pharmaceutical compositions, for the manufacture of medicaments for treating e.g. Chronic obstructive pulmonary disease (COPD), cystic fibrosis and asthma.

BRIEF DESCRIPTION OF THE DRAWINGS

FIG. 1 shows a characteristic X-ray powder diffraction pattern (XRPD) of Ensifentrine ethane-1,2-disulfonate Form ES1.

FIG. 2 shows a characteristic X-ray powder diffraction pattern (XRPD) of Ensifentrine ethane-1,2-disulfonate Form ES2.

FIG. 3 shows a characteristic X-ray powder diffraction pattern (XRPD) of Ensifentrine ethane-1,2-disulfonate Form ES3.

FIG. 4 shows a characteristic X-ray powder diffraction pattern (XRPD) of amorphous Ensifentrine ethane-1,2-disulfonate.

Figure 5A:
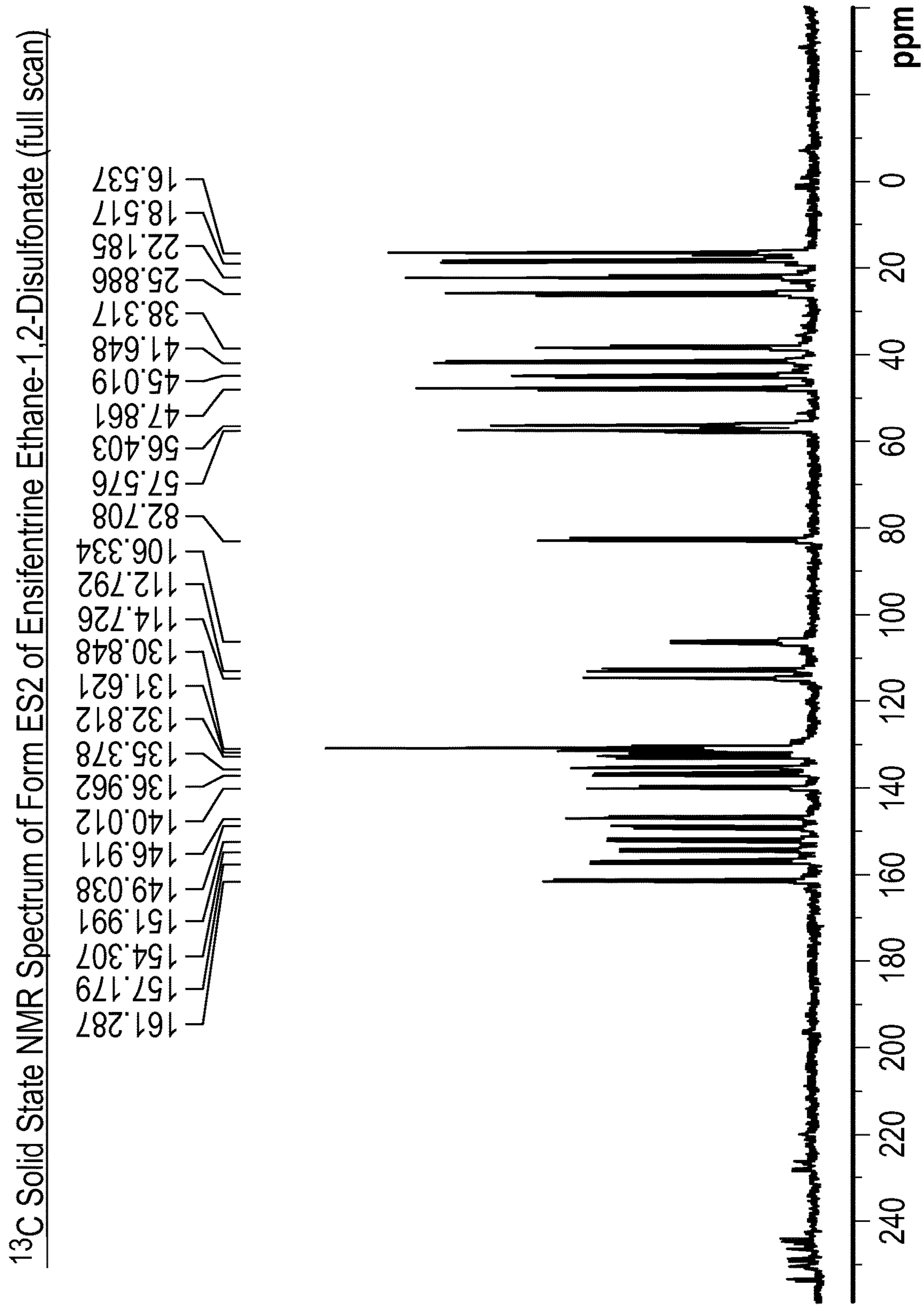

FIG. **5*a*** shows $^{13}C$ solid state NMR spectrum of Form ES2 of Ensifentrine ethane-1,2-disulfonate (full scan).

FIG. **5*b*** shows $^{13}C$ solid state NMR spectrum of Form ES2 of Ensifentrine ethane-1,2-disulfonate (at the range of 0-100 ppm).

FIG. **5*c*** shows $^{13}C$ solid state NMR spectrum of Form ES2 of Ensifentrine ethane-1,2-disulfonate (at the range of 100-200 ppm).

DETAILED DESCRIPTION OF THE DISCLOSURE

The present disclosure encompasses solid state forms of Ensifentrine and salts of Ensifentrine, particularly Ensifentrine ethane-1,2-disulfonate, including crystalline polymorphs of Ensifentrine and salts of Ensifentrine, particularly Ensifentrine ethane-1,2-disulfonate, processes for preparation thereof, and pharmaceutical compositions thereof. In embodiments, the present disclosure provides crystalline forms of Ensifentrine ethane-1,2-disulfonate designated as Form ES1, ES2 and Form ES3 (defined herein).

Solid state properties of Ensifentrine and salts of Ensifentrine, particularly Ensifentrine ethane-1,2-disulfonate and crystalline polymorphs thereof can be influenced by controlling the conditions under which Ensifentrine and salts of Ensifentrine, particularly Ensifentrine ethane-1,2-disulfonate and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Ensifentrine and salts of Ensifentrine, particularly Ensifentrine ethane-1,2-disulfonate described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Ensifentrine and salts of Ensifentrine, particularly Ensifentrine ethane-1,2-disulfonate. In some embodiments of the disclosure, the described crystalline polymorph of Ensifentrine and salts of Ensifentrine, particularly Ensifentrine ethane-1,2-disulfonate may contain from about 1% to about 20% (w/w), from about 5% to about 20% (w/w), or from about 5% to about 10% (w/w) of one or more other crystalline polymorph of the same Ensifentrine and salts of Ensifentrine, particularly Ensifentrine ethane-1,2-disulfonate. For example, a crystalline polymorph of Ensifentrine ethane-1,2-disulfonate according to any aspect or embodiment of the present invention may be polymorphically pure, and may contain: about 20% (w/w) or less, about 10% (w/w) or less, about 5% (w/w) or less, about 2% (w/w) or less, about 1% (w/w) or less, or about 0% of any other forms of Ensifentrine ethane-1,2-disulfonate, as measured, for example, by XRPD. Alternatively, a crystalline polymorph of Ensifentrine ethane-1,2-disulfonate according to any aspect or embodiment of the present invention may be polymorphically pure and may contain greater than about 80% (w/w), greater than about 90% (w/w), greater than about 95% (w/w), greater than about 98% (w/w), greater than about 99% (w/w), or about 100% of the crystalline polymorph of Ensifentrine ethane-1,2-disulfonate.

Depending on which other crystalline polymorphs a comparison is made, the crystalline polymorphs of Ensifentrine and salts of Ensifentrine, particularly Ensifentrine ethane-1,2-disulfonate of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Ensifentrine and salts of Ensifentrine, particularly Ensifentrine ethane-1,2-disulfonate referred to herein as being characterized by graphical data "as depicted in" or "as substantially depicted in" a Figure will thus be understood to include any crystal forms of Ensifentrine and salts of Ensifentrine, particularly Ensifentrine ethane-1,2-disulfonate characterized with the graphical data having such small variations, as are well known to the skilled person, in comparison with the Figure.

As used herein, and unless stated otherwise, the term "anhydrous" in relation to crystalline forms of Ensifentrine and salts of Ensifentrine, particularly Ensifentrine ethane-1,2-disulfonate, relates to a crystalline form of Ensifentrine and salts of Ensifentrine, particularly Ensifentrine ethane-1,2-disulfonate which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to crystalline polymorph of Ensifentrine and salts of Ensifentrine, particularly Ensifentrine ethane-1,2-disulfonate of the present disclosure corresponds to a crystalline polymorph of Ensifentrine and salts of Ensifentrine, particularly Ensifentrine ethane-1,2-disulfonate that is physically separated from the reaction mixture in which it is formed.

As used herein, unless stated otherwise, the XRPD measurements are taken using copper Kα radiation wavelength 1.5418 Å. XRPD peaks reported herein are measured using CuKα radiation, λ=1.5418 Å, typically at a temperature of 25±3° C.

As used herein, unless stated otherwise, $^{13}C$ NMR reported herein are measured at 11.7 T at a magic angle spinning frequency $\omega_r/2\pi$=15 kHz, preferably at a temperature of at 300 K±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Ensifentrine ethane-1,2-disulfonate, designated ES1. The crystalline Form ES1 of Ensifentrine ethane-1,2-disulfonate may be characterized by data selected from one or more of the following: an X-ray powder diffraction pattern substantially as depicted in FIG. 1; an X-ray powder diffraction pattern having peaks at 10.4, 15.8, 19.6, 21.5 and 26.0 degrees 2-theta±0.2 degrees 2-theta; and combinations of these data.

Crystalline Form ES1 of Ensifentrine ethane-1,2-disulfonate may be further characterized by an X-ray powder diffraction pattern having peaks at 10.4, 15.8, 19.6, 21.5 and 26.0 degrees 2-theta±0.2 degrees 2-theta, and also having any one, two, three, or four additional peaks selected from 8.6, 9.2, 14.4 and 31.0 degrees 2-theta±0.2 degrees 2-theta.

Crystalline Form ES1 of Ensifentrine ethane-1,2-disulfonate may be alternatively characterized by an X-ray powder diffraction pattern having peaks at 8.6, 9.2, 10.4, 14.4, 15.8, 19.6, 21.5, 26.0 and 31.0 degrees 2-theta±0.2 degrees 2-theta.

In one embodiment of the present disclosure, crystalline Form ES1 of Ensifentrine ethane-1,2-disulfonate is isolated.

Crystalline Form ES1 of Ensifentrine ethane-1,2-disulfonate may be hydrate form.

Crystalline Form ES1 of Ensifentrine ethane-1,2-disulfonate may be characterized by each of the above characteristics alone/or by all possible combinations, e.g., an XRPD pattern having peaks at 10.4, 15.8, 19.6, 21.5 and 26.0 degrees 2-theta±0.2 degrees 2-theta; an XRPD pattern as depicted in FIG. 1, and combinations thereof.

Crystalline Form ES1 of Ensifentrine ethane-1,2-disulfonate as described in any embodiment herein may be polymorphically pure.

Figure 5B:
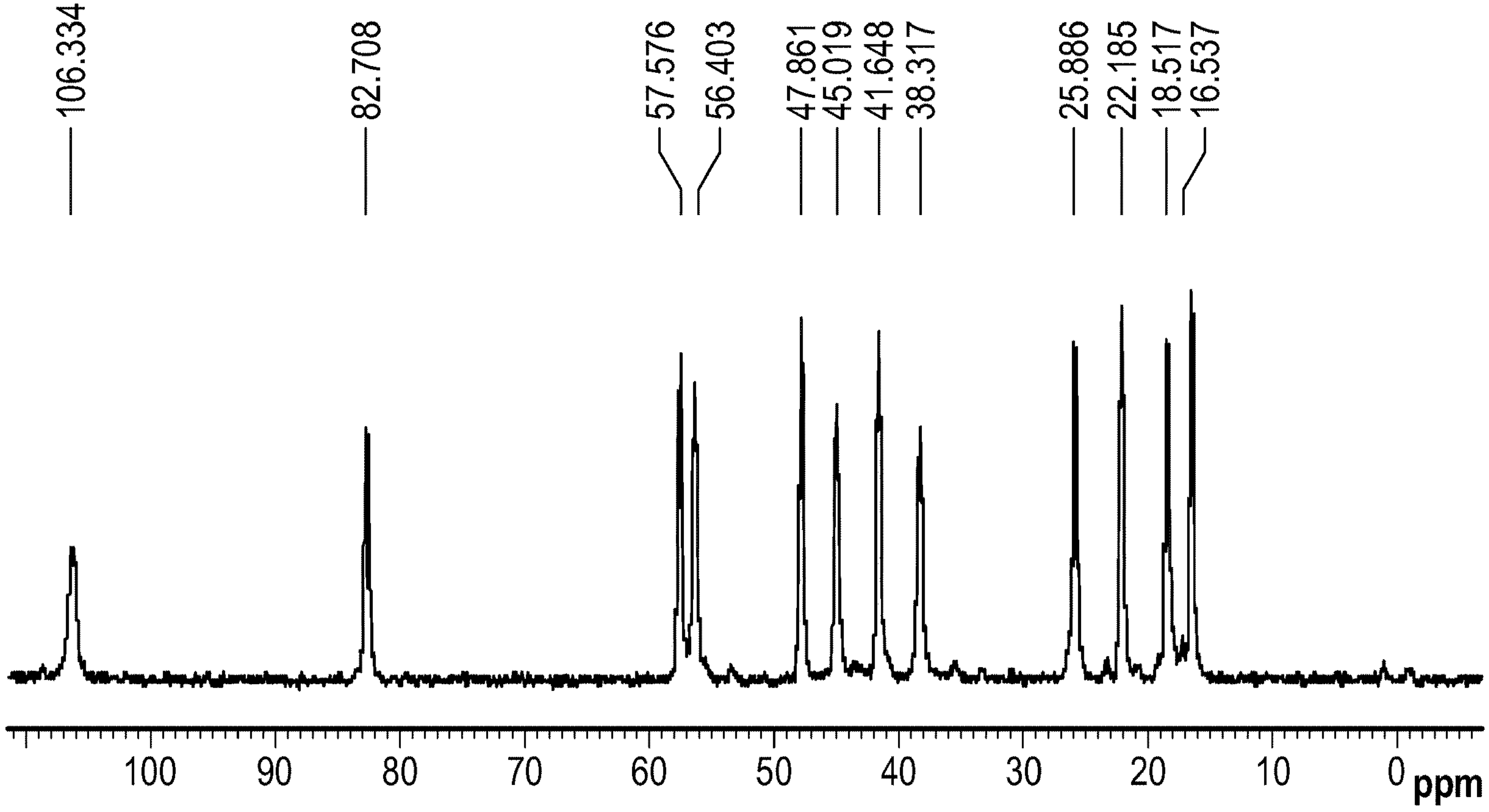
Figure 5C:
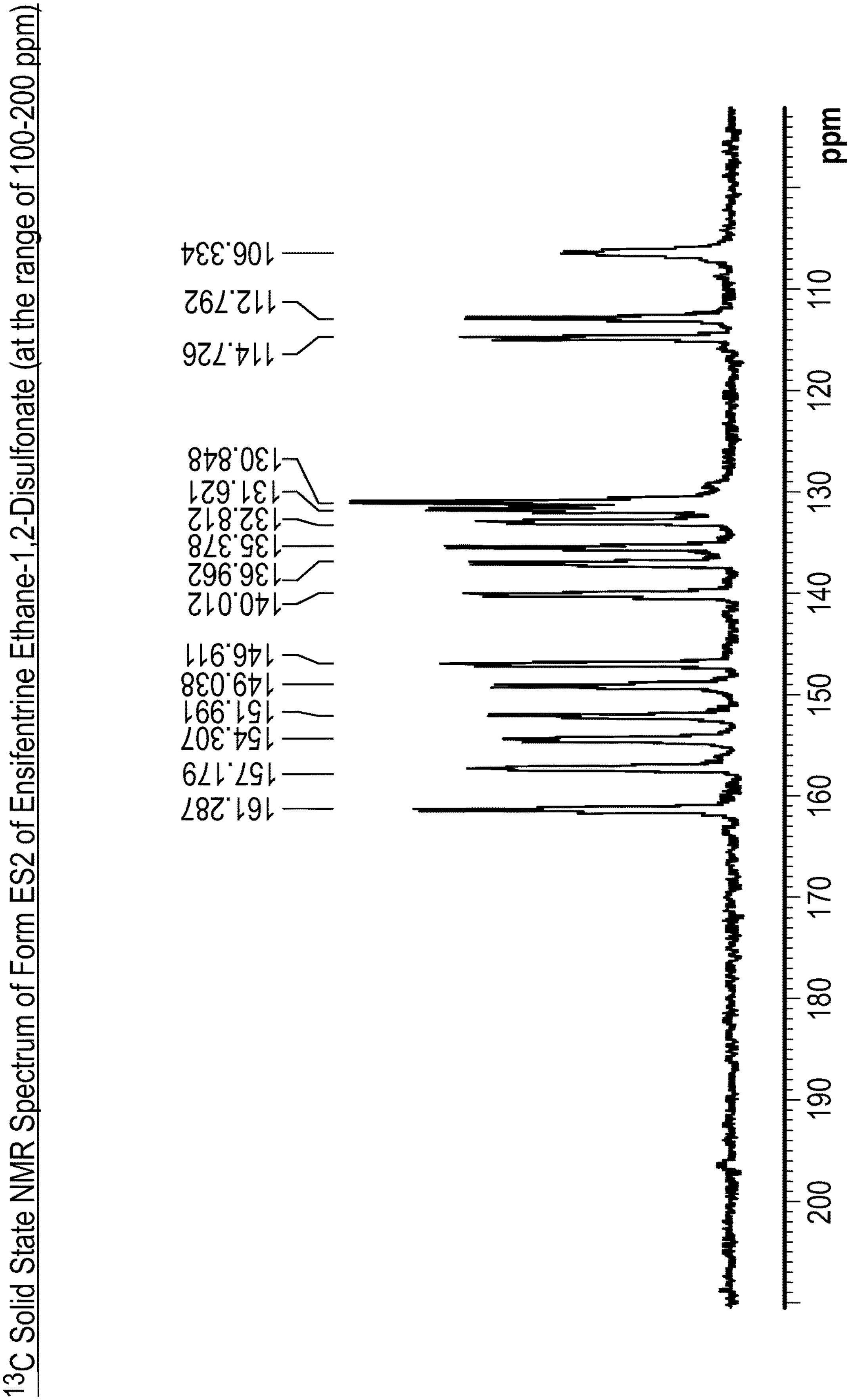

The present disclosure includes a crystalline polymorph of Ensifentrine ethane-1,2-disulfonate, designated ES2. The crystalline Form ES2 of Ensifentrine ethane-1,2-disulfonate may be characterized by data selected from one or more of the following: an X-ray powder diffraction pattern substantially as depicted in FIG. 2; an X-ray powder diffraction pattern having peaks at 14.4, 19.0, 19.7, 26.1 and 31.1 degrees 2-theta±0.2 degrees 2-theta; a solid state $^{13}C$ NMR spectrum having peaks at 45.0, 112.8, 140.0, 146.9, 157.2 and 161.3 ppm±0.2 ppm; a solid state $^{13}C$ NMR spectrum having the following chemical shift absolute differences from a reference peak at 41.7 ppm±2 ppm of 3.3, 71.1, 98.3, 105.2, 115.5 and 119.6 ppm±0.1 ppm; a solid state $^{13}C$ NMR spectrum substantially as depicted in FIG. 5*a*, 5*b* or 5*c*; and combinations of these data.

Crystalline Form ES2 of Ensifentrine ethane-1,2-disulfonate may be further characterized by an X-ray powder diffraction pattern having peaks at 14.4, 19.0, 19.7, 26.1 and 31.1 degrees 2-theta±0.2 degrees 2-theta, and also having any one, two, three, or four additional peaks selected from 10.4, 17.2, 21.6 and 29.4 degrees 2-theta±0.2 degrees 2-theta.

Crystalline Form ES2 of Ensifentrine ethane-1,2-disulfonate may be alternatively characterized by an X-ray powder diffraction pattern having peaks at 10.4, 14.4, 17.2, 19.0, 19.7, 21.6, 26.1, 29.4 and 31.1 degrees 2-theta±0.2 degrees 2-theta.

In one embodiment of the present disclosure, crystalline Form ES2 of Ensifentrine ethane-1,2-disulfonate is isolated.

Crystalline Form ES2 of Ensifentrine ethane-1,2-disulfonate may be hydrate form. The hydrate may have water content of about 5% to about 6% measured by KF and TGA.

Crystalline Form ES2 of Ensifentrine ethane-1,2-disulfonate may have stoichiometry of Ensifentrine: ethane-1,2-disulfonic acid of about 2:1.

Crystalline Form ES2 of Ensifentrine ethane-1,2-disulfonate may be characterized by each of the above characteristics alone/or by all possible combinations, e.g., an XRPD pattern having peaks at 14.4, 19.0, 19.7, 26.1 and 31.1 degrees 2-theta±0.2 degrees 2-theta; an XRPD pattern as depicted in FIG. 2, and combinations thereof.

In specific embodiment, the present disclosure includes Crystalline Form ES2 of Ensifentrine ethane-1,2-disulfonate which is polymorphically pure; i.e., it is substantially free of any other forms, as described herein above. Accordingly, Crystalline Form ES2 of Ensifentrine ethane-1,2-disulfonate as described in any embodiment of the present disclosure may be substantially free of other solid state forms of Ensifentrine ethane-1,2-disulfonate. Particularly, it is substantially free of Crystalline Form ES1 of Ensifentrine ethane-1,2-disulfonate.

Accordingly, the content of Crystalline Form ES1 of Ensifentrine ethane-1,2-disulfonate in Crystalline Form ES2 of Ensifentrine ethane-1,2-disulfonate will be measured by detecting peaks of Crystalline Form ES1 of Ensifentrine ethane-1,2-disulfonate which are absent in Crystalline Form ES2 of Ensifentrine ethane-1,2-disulfonate.

The present disclosure further comprises a process for preparation of Form ES2 of Ensifentrine ethane-1,2-disulfonate. The process may comprise crystallisation of Ensifentrine ethane-1,2-disulfonate from a mixture of dimethyl acetamide (DMAc), ethanol, water and methyl tert-butyl ether (MTBE).

The process may particularly comprise:

(a) combining a solution of Ensifentrine ethane-1,2-disulfonate in dimethyl acetate and ethanol, preferably at a temperature of about 40° C. to about 100° C., with a mixture of water and methyl tert-butyl ether, (b) optionally isolating Ensifentrine form ES2 form 2; and (c) optionally drying.

According to any embodiment of the process, the solution of Ensifentrine ethane-1,2-disulfonate, DMAc and ethanol is heated to a temperature of: about 40° C. to about 100° C., about 45° C. to about 90° C., about 50° C. to about 80° C., about 55° C. to about 70° C., or about 60° C. to about 65° C.

According to any embodiment of the process, DMAc may be used in an amount of: about 10 ml to about 100 ml, about 20 ml to about 60 ml, about 30 ml to about 50 ml, about 35 ml to about 45 ml, or about 40 ml, per gram of Ensifentrine.

According to any embodiment of the process, ethanol may be used in an amount of: about 5 ml to about 40 ml, about 5 ml to about 30 ml, about 5 ml to about 20 ml, about 8 ml to about 18 ml, about 10 ml to about 15 ml, or about 12 ml, per gram of Ensifentrine.

According to any embodiment of the process, the volume ratio of ethanol to DMAc may be: about 1:1 to about 1:8, about 1:1.5 to about 1:6, about 1:1.8 to about 1:5, about 1:2 to about 1:4, about 1:3 to about 1:3.5 or about 1:3.3.

According to any embodiment of the process, the water and MTBE are premixed before combining with the solution of Ensifentrine ethane-1,2-disulfonate in DMAc and ethanol in step (a). The water may be used in an amount of: about 4 ml to about 40 ml, about 5 ml to about 30 ml, about 6 ml to about 20 ml, about 7 ml to about 15 ml, about 8 ml to about 12 ml, or about 10 ml, per gram of Ensifentrine. The MTBE in the mixture of water and MTBE may be used in an amount of: about 50 ml to about 120 ml, about 60 ml to about 110 ml, about 70 ml to about 105 ml, about 80 ml to about 100 ml, about 85 ml to about 95 ml, or about 90 ml, per gram of Ensifentrine. The ratio of mixture of water to MTBE in the mixture of water and MTBE may be: about 1:5 to about 1:13, about 1:6 to about 1:12, about 1:7 to about 1:11, about 1:8 to about 1:10, about 1:8.5 to about 1:9.5 or about 1:9.

According to any embodiment of the process, the premixture of water and MTBE is added to the solution of Ensifentrine ethane-1,2-disulfonate in DMAc and ethanol in step (a). Preferably, the addition is carried out under heating, preferably to a temperature of: about 40° C. to about 100° C., about 45° C. to about 90° C., about 50° C. to about 80° C., about 55° C. to about 70° C., or about 60° C. to about 65° C.

According to any embodiment of the process, the combining of the water/MTBE with the solution of Ensifentrine ethane-1,2-disulfonate in DMAc and ethanol in step (a) initiates crystallisation of the Ensifentrine ethane-1,2-disulfonate.

According to any embodiment of the process, a further amount of MTBE antisolvent may optionally be added to the mixture. Preferably, this MTBE is used in amount of: about 10 ml to about 100 ml, about 20 ml to about 80 ml, about 30 ml to about 70 ml, about 40 ml to about 60 ml, about 45 ml to about 55 ml, or about 50 ml, per gram of Ensifentrine. Preferably, according to any embodiment of the process, the total amount of MTBE used is: about 70 ml to about 200 ml, about 90 ml to about 180 ml, about 110 ml to about 170 ml, about 120 ml to about 160 ml, about 130 ml to about 150 ml, about 135 ml to about 145 ml, or about 140 ml, per gram of Ensifentrine.

According to any embodiment of the process, the mixture in step (a) may be cooled after the addition of water/MTBE, or after the optional addition of the further amount of MTBE. Preferably, the cooling may be to a temperature of: about 0° C. to about 30° C., about 5° C. to about 28° C., about 10° C. to about 28° C., about 15° C. to about 25° C., or about 20° C. to about 25° C.

Optionally, according to any embodiment of the process, the reaction mixture may be maintained at the cooled temperature for a period of: about 1 to about 24 hours, about 4 to about 18 hours, about 6 to about 15 hours, or about 8 to about 10 hours.

Optionally, the Ensifentrine ethane-1,2-disulfonate form ES2 may be isolated, preferably by any suitable procedure, such as decantation, centrifuge or filtration, preferably by filtration.

The Ensifentrine ethane-1,2-disulfonate form ES2 may be optionally dried, for example, by air flow during filtration, and/or under reduced pressure (vacuum drying). Vacuum drying may be conducted at temperature of: about 40° C. to about 80° C., about 50° C. to about 70° C., about 55° C. to about 65° C., or about 60° C. The drying may be carried out for a suitable time to remove the solvents, optionally for about 0.5 to about 4 hours, about 0.5 to about 2 hours, about 0.5 to about 1.5 hours, or about 1 hour.

Optionally, the solution of Ensifentrine-1,2-ethane disulfonate in DMAc and ethanol in step (a) may prepared by a process comprising providing a solution of Ensifentrine in DMAc, preferably at a temperature of about 40° C. to about 100° C.; and combining with a solution of ethane-1,2-disulfonic acid in ethanol. The amounts and ratios of DMAc and ethanol are preferably as discussed above. Preferably, the temperature of the solution of Ensifentrine in DMAc is: about 40° C. to about 100° C., about 45° C. to about 90° C., about 50° C. to about 80° C., about 55° C. to about 70° C., or about 60° C. to about 65° C.

Preferably, ethane-1,2-disulfonic acid is used in amount of: about 1.9 to about 2.5 mole equivalents, about 2.0 to about 2.3 mole equivalents, about 2.0 to about 2.2 mole equivalents, about 2.1 mole equivalents, or about 2 mole equivalents, per mole of Ensifentrine.

In accordance with any embodiment of the process, form ES2 of Ensifentrine may be prepared by a process comprising:

(i) providing a solution of Ensifentrine in DMAc;
(ii) adding ethane-1,2-disulfonic acid in ethanol;
(iii) combining the solution with pre-mixed water and MTBE;
(iv) cooling the reaction mixture;
(v) optionally maintaining the mixture for suitable period of time;
(vi) optionally isolating Form ES2 of Ensifentrine; and
(vii) optionally drying the Form ES2 of Ensifentrine.

In any embodiment of this process, the solution in step (i) may be prepared by dissolving Ensifentrine in DMAc. The DMAc may be dissolved at an elevated temperature, preferably at a temperature of: about 35° C. to about 90° C., about 45° C. to about 80° C., about 55° C. to about 75° C., or about 60° C. to about 65° C. According to any aspect or embodiment of the process, the DMAc may be used in an amount of about 20 ml to about 80 ml, about 30 ml to about 70 ml, about 35 ml to about 55 ml, or about 40 ml, per gram of Ensifentrine. Step (ii) may comprise adding a solution of ethane-1,2-disulfonic acid in ethanol. Preferably step (ii) comprises maintaining ethane-1,2-disulfonic acid in ethanol at a temperature of: about 35° C. to about 90° C., about 45° C. to about 80° C., about 55° C. to about 75° C., or about 60° C. to about 65° C. for period of about 1 hour to 15 minutes, or about 30 minutes. According to any aspect or embodiment of the process, the ethanol may be used in an amount of about 20 ml to about 80 ml, about 20 ml to about 70 ml, about 25 ml to about 55 ml, or about 30 ml, per gram of ethane-1,2-disulfonic acid. According to any aspect or embodiment of the process, the ethane-1,2-disulfonic acid in ethanol may be used in an amount of about 5 ml to about 20 ml, about 8 ml to about 18 ml, about 10 ml to about 15 ml, or about 12 ml, per gram of Ensifentrine. According to any aspect or embodiment of the process, the Pre-mixed water and MTBE in step (iii) may be added at a temperature of about 35° C. to about 90° C., about 45° C. to about 80° C., about 55° C. to about 75° C., or about 60° C. to about 65° C. According to any aspect or embodiment of the process, pre-mixed water and MTBE is preferably used in an amount of about 40 ml to about 300 ml, about 60 ml to about 250 ml, about 80 ml to about 220 ml, about 90 ml to about 200 ml, about, or about 100 ml, per gram of Ensifentrine. According to any aspect or embodiment of the process, pre-mixed water and MTBE is preferably used in ratio of about 10:90. According to any aspect or embodiment of the process, MTBE is additionally used in an amount of about 30 ml to about 100 ml, about 40 ml to about 80 ml, or about 50 ml, per gram of Ensifentrine to get the precipitation. The process may further comprise cooling according to step (iv) at the temperature of about 10° C. to about 40° C., about 15° C. to about 30° C., or about 20° C. to about 25° C. The mixture may be stirred, and maintained for a period of about 6 hours to about 15 hours, about 8 hour to about 13 hours, or about 12 hours. The ES2 Form of Ensifentrine ethane-1,2-disulfonate may be isolated, preferably by any suitable process, such as decantation, filtration or by centrifuge, preferably by filtration. The filtering may be carried out at a temperature of about 10° C. to about 40° C., about 15° C. to about 30° C., or about 25° C.

In any embodiment of this process, the crystalline Ensifentrine Form ES2 may be dried. The crystalline Ensifentrine ethane-1,2-disulfonate Form ES2 may be dried, typically at a temperature of about 20° C. to about 60° C., about 25° C. to about 55° C., about 25° C. The drying may be carried out for any suitable time to remove the solvent, typically about 1 to about 5 hours, about 1.5 hours to about 4 hours, or about 2 hours to about 3 hours, or about 15 minutes to about 20 minutes. The crystalline Form ES2 of Ensifentrine ethane-1,2-disulfonate may be dried under vacuum, typically at a temperature of about 40° C. to about 80° C., about 50° C. to about 70° C., about 60° C. The drying may be carried out for any suitable time to remove the solvent, typically about 1 to about 5 hours, about 1.5 hours to about 4 hours, or about 2 hours. After isolating, the Form ES2 of Ensifentrine ethane-1,2-disulfonate may be dried. The drying may be conducted at reduced pressure or under vacuum. The drying may be conducted at reduced pressure at any suitable temperature, particularly at: about 20° C. to about 40° C., about 22° C. to about 30° C., or about 25° C. The drying may be conducted for a suitable period of time to remove the solvents, preferably for: about 0.5 hours to about 6 hours, about 1 hour to about 5 hours, about 15 minutes to 20 minutes. The drying may be conducted under vacuum at any suitable temperature, particularly at: about 40° C. to about 80° C., about 45° C. to about 75° C., or about 60° C. The drying may be conducted for a suitable period of time to remove the solvents, preferably for: about 0.5 hours to about 2 hours, or about 1 hour.

According to any aspect or embodiment of the disclosure, the processes for preparing Ensifentrine ethane-1,2-disulfonate form ES2, the process may further comprise combining the Ensifentrine ethane-1,2-disulfonate form ES2 with at least one pharmaceutically acceptable excipient to prepare a pharmaceutical composition. Optionally, the process as described in any aspect or embodiment of the disclosure, the process may optionally comprise converting the Ensifentrine ethane-1,2-disulfonate form ES2 into another solid state form of Ensifentrine ethane-1,2-disulfonate, or Ensifentrine base, or another Ensifentrine salt, and combining the solid state form of Ensifentrine ethane-1,2-disulfonate, or Ensifentrine base, or another Ensifentrine salt, with at least one pharmaceutically acceptable excipient to form a pharmaceutical composition.

The present disclosure further encompasses Ensifentrine ethane-1,2-disulfonate dihydrate.

The present disclosure includes a crystalline polymorph of Ensifentrine ethane-1,2-disulfonate, designated ES3. The crystalline Form ES3 of Ensifentrine ethane-1,2-disulfonate may be characterized by data selected from one or more of the following: an X-ray powder diffraction pattern substantially as depicted in FIG. 3; an X-ray powder diffraction pattern having peaks at 4.6, 9.2, 11.9, 18.5 and 22.3 degrees 2-theta±0.2 degrees 2-theta; and combinations of these data.

Crystalline Form ES3 of Ensifentrine ethane-1,2-disulfonate may be further characterized by an X-ray powder diffraction pattern having peaks at 4.6, 9.2, 11.9, 18.5 and 22.3 degrees 2-theta±0.2 degrees 2-theta, and also having any one, two, three, or four additional peaks selected from 13.8, 15.8, 23.3 and 23.9 degrees 2-theta±0.2 degrees 2-theta.

Crystalline Form ES3 of Ensifentrine ethane-1,2-disulfonate may be alternatively characterized by an X-ray powder diffraction pattern having peaks at 4.6, 9.2, 11.9, 13.8, 15.8, 18.5, 22.3, 23.3 and 23.9 degrees 2-theta±0.2 degrees 2-theta.

In one embodiment of the present disclosure, crystalline Form ES3 of Ensifentrine ethane-1,2-disulfonate is isolated.

Crystalline Form ES3 of Ensifentrine ethane-1,2-disulfonate may be characterized by each of the above characteristics alone/or by all possible combinations, e.g., an XRPD pattern having peaks 4.6, 9.2, 11.9, 18.5 and 22.3 degrees 2-theta±0.2 degrees 2-theta; an XRPD pattern as depicted in FIG. 3, and combinations thereof.

In specific embodiments, the present disclosure includes Crystalline Form ES3 of Ensifentrine ethane-1,2-disulfonate which is polymorphically pure; i.e., it is substantially free of any other forms, as described herein above. Particularly, it is substantially free of Crystalline Form ES1 of Ensifentrine ethane-1,2-disulfonate.

Accordingly, the content of Crystalline Form ES1 of Ensifentrine ethane-1,2-disulfonate in Crystalline Form ES3 of Ensifentrine ethane-1,2-disulfonate will be measured by detecting peaks of Crystalline Form ES1 of Ensifentrine ethane-1,2-disulfonate which are absent in Crystalline Form ES3 of Ensifentrine ethane-1,2-disulfonate.

Any of the crystalline polymorphs of Ensifentrine or Ensifentrine salts, particularly Ensifentrine ethane-1,2-disulfonate, may be provided in polymorphically pure form.

The above crystalline polymorphs can be used to prepare other crystalline polymorphs of Ensifentrine, Ensifentrine salts, particularly Ensifentrine ethane-1,2-disulfonate and their solid state forms.

The present disclosure encompasses a process for preparing other solid state forms of Ensifentrine, Ensifentrine salts, particularly Ensifentrine ethane-1,2-disulfonate and their solid state forms thereof.

The present disclosure provides the above described crystalline polymorphs of Ensifentrine, Ensifentrine salts, particularly Ensifentrine ethane-1,2-disulfonate for use in the preparation of pharmaceutical compositions comprising Ensifentrine, Ensifentrine salts, particularly Ensifentrine ethane-1,2-disulfonate and/or crystalline polymorphs thereof.

The present disclosure also encompasses the use of crystalline polymorphs of Ensifentrine and salts of Ensifentrine, particularly Ensifentrine ethane-1,2-disulfonate of the present disclosure for the preparation of pharmaceutical compositions of crystalline polymorph Ensifentrine and salts of Ensifentrine, particularly Ensifentrine ethane-1,2-disulfonate and/or crystalline polymorphs thereof.

The present disclosure includes processes for preparing the above mentioned pharmaceutical compositions. The processes includes combining any one or a combination of the crystalline polymorphs of Ensifentrine and salts of Ensifentrine, particularly Ensifentrine ethane-1,2-disulfonate of the present disclosure with at least one pharmaceutically acceptable excipient.

Pharmaceutical combinations or formulations of the present disclosure contain any one or a combination of the solid state forms of Ensifentrine and salts of Ensifentrine, particularly Ensifentrine ethane-1,2-disulfonate of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Ensifentrine and salts of Ensifentrine, particularly Ensifentrine ethane-1,2-disulfonate and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs. The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Ensifentrine and salts of Ensifentrine, particularly Ensifentrine ethane-1,2-disulfonate can be administered. Ensifentrine and salts of Ensifentrine, particularly Ensifentrine ethane-1,2-disulfonate may be formulated for administration to a mammal, in embodiments to a human, by injection. Ensifentrine and salts of Ensifentrine, particularly Ensifentrine ethane-1,2-disulfonate can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Ensifentrine and salts of Ensifentrine, particularly Ensifentrine ethane-1,2-disulfonate and the pharmaceutical compositions and/or formulations of Ensifentrine and salts of Ensifentrine, particularly Ensifentrine ethane-1,2-disulfonate of the present disclosure can be used as medicaments, in embodiments in the treatment of Chronic obstructive pulmonary disease (COPD), cystic fibrosis and asthma.

The present disclosure also provides methods of treating Chronic obstructive pulmonary disease (COPD), cystic fibrosis and asthma by administering a therapeutically effective amount of any one or a combination of the crystalline polymorphs of Ensifentrine and salts of Ensifentrine, particularly Ensifentrine ethane-1,2-disulfonate of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction ("XRPD") Method

X-ray diffraction was performed on X-Ray powder diffractometer:

Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring with silicon low background.

All X-Ray Powder Diffraction peak values are calibrated with regard to standard silicon spiking in the sample.

SSNMR Method:

Solid-state NMR spectra were measured at 11.7 T using a Bruker Avance III HD 500 US/WB NMR spectrometer (Karlsruhe, Germany, 2013) with 3.2 mm probehead. The $^{13}C$ CP/MAS NMR spectra employing cross-polarization were acquired using the standard pulse scheme at spinning frequency of 15 kHz and a room temperature (300 K). The recycle delay was 8 s and the cross-polarization contact time was 2 ms. The $^{13}C$ scale was referenced to α-glycine (176.03 ppm for $^{13}C$). Frictional heating of the spinning samples was offset by active cooling, and the temperature calibration was performed with Pb(NO3)2. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δυ1/2 was less than 3.5 Hz at 250 ms of acquisition time).

EXAMPLES

Preparation of Starting Materials

Ensifentrine can be prepared according to methods known from the literature, for example U.S. Pat. Nos. 6,794,391 and 9,062,047. Ensifentrine ethane-1,2-disulfonate can be prepared according to methods known from the literature, for example U.S. Pat. No. 10,463,665.

Example 1: Preparation of ensifentrine ethane-1,2-disulfonate Form ES1

Ensifentrine (1.0 gram) was taken in a 250 mL RB flask and was suspended in 40 mL of DMAc at temperature of about 60° C. The suspension was stirred at 60° C. for about 20 minutes to 30 minutes. Clear solution was observed. To this clear solution, 12 mL of ethane-1,2-disulfonic acid (1 gram in 30 mL ethanol) was added. Then this clear solution was maintained under stirring at temperature of about 60° C. for period of about 1 hour. 50 mL of MTBE was added to it, then precipitation was observed and was cooled to about 20° C. to about 25° C. and maintained for period of about 1 hour. Then this reaction mixture was filtered at temperature of about 25° C. under vacuum and suck dried for period of 15 minutes to about 20 minutes at temperature of about 25° C. The obtained solid was dried under vacuum at temperature of about 60° C. for period of about 3 hours and was analyzed by XRPD. Form ES1 was obtained. An XRPD Pattern is shown in FIG. 1.

Example 2: Preparation of ensifentrine ethane-1,2-disulfonate Form ES2

Ensifentrine (1.0 gram) was taken in a 250 mL RB flask and was suspended in 40 mL of DMAc at temperature of about 60° C. to about 65° C. The suspension was stirred at temperature of about 60° C. to about 65° C. for about 20 minutes to 30 minutes. Clear solution was observed. To this clear solution, 12 mL of ethane-1,2-disulfonic acid (400 mg in 12 mL ethanol) was added. Then this solution was maintained under stirring at temperature of about 60° C. to about 65° C. for period of 30 minutes. Pre-mixed water and MTBE (10:90) 100 mL was added to this reaction mixture and precipitation was started. Then additional 50 ml MTBE charged to the reaction mixture and was cooled to about 20° C. to about 25° C. and maintained for overnight. Then this reaction mixture was filtered at temperature of about 25° C. under vacuum and suck dried at temperature of about 25° C. for period of about 15 minutes to about 20 minutes. The obtained solid was dried under vacuum at temperature of about 60° C. for period of about 1 hour and was analyzed by XRPD. Form ES2 was obtained. An XRPD Pattern is shown in FIG. 2

Example 3: Preparation of ensifentrine ethane-1,2-disulfonate Form ES3

Ensifentrine 1,2-ethane disulfonate amorphous form (0.84 grams) was taken in a 100 mL RB flask and was suspended in 42 mL of diacetone alcohol at temperature of about 60° C. to about 65° C. The suspension was stirred at temperature of about 60° C. to about 65° C. for period of about 10 minutes to about 15 minutes to prepare clear stock solution. In 10 ml test tube, 4 mL of tertiary amyl alcohol was taken and maintained under stirring at temperature of about 0° C. to about 5° C. for period of about 18 hours. 1 mL of stock solution was charged into pre cooled test tube containing 4 mL of tertiary amyl alcohol at temperature of about 0° C. to about 5° C. and was stirred overnight at temperature of about 0° C. to about 5° C. The obtained solid was filtered at temperature of about 25° C. under vacuum and suck dried for period of about 15 minutes to about 20 minutes. The obtained solid was analyzed by XRPD. Form ES3 was obtained. An XRPD Pattern is shown in FIG. 3.

Example 4: Preparation of ensifentrine ethane-1,2-disulfonate Form ES3

Ensifentrine 1,2-ethane disulfonate amorphous form (0.5 grams) was taken in a 50 mL flask and was suspended in 20 mL of diacetone alcohol at temperature of about 60° to about 65° C. The suspension was stirred at temperature of about 60° C. to about 65° C. for about for period of about 10 minutes to about 15 minutes to prepare clear stock solution. In 250 mL RB flask, about 60 mL of dibutyl ether was taken and maintained under stirring at temperature of about 0° C. to about 5° C. for period of about one hour. 20 mL of stock solution was charged into pre cooled 250 mL RB flask containing 60 mL of Di butyl ether at temperature of about 0° C. to about 5° C. and stirred for about one hour to about 2 hours. The obtained solid was maintained under stirring for 4 hours at temperature of about 0° C. to about 5° C. and was filtered at temperature of about 25° C. under vacuum and suck dried for period of about 15 minutes to about 20 minutes. The obtained solid was dried in vacuum tray dryer at temperature of about 60° C. for period of about 3 hours. The obtained solid was analyzed by XRPD. Form ES3 was obtained.

Example 5: Preparation of Amorphous ensifentrine ethane-1,2-disulfonate

Ensifentrine 1,2-ethane disulfonate (3.0 grams) was taken in a 500 mL Rota evaporation flask and was dissolved in 150 mL Dichloromethane:Methanol (20:80) at temperature of about 40° C. to about 50° C. The obtained Clear solution was filtered to remove undissolved material if any and was distilled under vacuum at temperature of 40° C. to about 50° C. for period of about 10 minutes to about 15 minutes. Solid was observed after distillation and washed with diisopropylether (DIPE) and filtered under vacuum at temperature of about 25° C. for period of about 15 minutes to about 20 minutes. The obtained solid was again dissolved in 150 mL Dichloromethane:Methanol (20:80) at temperature of about 40° C. to about 50° C. Filtered the solution to remove undissolved material if any and was distilled under vacuum at temperature of 40° C. to about 50° C. for about 30 minutes. The obtained solid was suspended in 50 mL diethyl ether and this suspension was filtered under vacuum at temperature of about 25° C. period of about 15 minutes to about 20 minutes. The obtained solid was isolated and was analyzed by XRPD. Amorphous form of Ensifentrine ethane-1,2-disulfonate was obtained. An XRPD Pattern is shown in FIG. 4.

Example 6: Stability Experiments

Storage Stability at Different Relative Humidities

Samples of Ensifentrine ethane-1,2-disulfonate form ES2 were subjected to conditions of different relative humidities at ambient temperature. XRPD analysis was performed on the samples after 7 days. The results are shown in Table 1 below:

TABLE 1

| Ensifentrine ethane-1,2-disulfonate | Relative humidity | | | | |
|---|---|---|---|---|---|
| Form ES2 | 20% | 40% | 60% | 80% | 100% |
| XRPD analysis results | No change | No change | No change | No change | No change |

These results demonstrate that Form ES2 of Ensifentrine ethane-1,2-disulfonate is stable after exposure to high and low relative humidity for at least 7 days.

Samples of Ensifentrine ethane-1,2-disulfonate form ES2 were subjected to conditions of different relative humidities at different temperatures. XRPD analysis was performed on the samples after 6 months. The results are shown in Table 2 below:

TABLE 2

| Ensifentrine ethane- | Conditions (6 months) | |
|---|---|---|
| 1,2-disulfonate Form ES2 | 25° C., 60% RH | 40° C., 75% RH |
| XRPD analysis results | No change | No change |

The results demonstrate that Form ES2 of Ensifentrine ethane-1,2-disulfonate is stable after exposure to high and low relative humidity at different temperatures for at least 6 months, indicating that this crystalline form has good storage stability.

Grinding Experiments

Samples of Ensifentrine ethane-1,2-disulfonate form ES2 were subjected to strong grinding, and to solvent drop grinding in water and ethanol. Grinding was carried out on the samples alone, or in the presence of ethanol or water. In these experiments, about 20 mg of the sample is placed in a mortar and ground with a pestle for 2 minutes. The solvent, when used, as added to the crystalline material before grinding, in a volume of 10 microlitres. XRPD analysis performed on each of the samples after the grinding experiment, confirmed no change in the starting material (Table 3):

TABLE 3

| Ensifentrine ethane-1,2-disulfonate form ES2 | |
|---|---|
| Condition | XRPD analysis results |
| Strong grinding | No change |
| Solvent-drop grinding (ethanol) | No change |
| Solvent-drop grinding (water) | No change |

The results demonstrate that Ensifentrine ethane-1,2-disulfonate form ES2 is resistant to polymorphic changes and is highly suitable for preparing pharmaceutical formulations.

Thermal Stability

A sample of Ensifentrine ethane-1,2-disulfonate form ES2 was subjected to heating up to 100° C. for 30 minutes. XRPD analysis of the sample confirmed no change in the starting material (Table 4):

TABLE 4

| Ensifentrine ethane-1,2-disulfonate form ES2 | |
|---|---|
| Condition | Result |
| Heating 100° C., 30 minutes | Stable |

The invention claimed is:

1. Crystalline Form ES2 of Ensifentrine ethane-1,2-disulfonate characterized by data selected from at least one of:

a) an XRPD pattern having peaks at 14.4, 19.0, 19.7, 26.1 and 31.1 degrees 2-theta±0.2 degrees 2-theta;

b) a solid state $^{13}C$ NMR spectrum having peaks at 45.0, 112.8, 140.0, 146.9, 157.2 and 161.3 ppm±0.2 ppm; or c) a solid state $^{13}C$ NMR spectrum having the following chemical shift absolute differences from a reference peak at 41.7 ppm±2 ppm of 3.3, 71.1, 98.3, 105.2, 115.5 and 119.6 ppm±0.1 ppm and d) combinations of (a) with (b), (a) with (c), or (b) with (c).

2. Crystalline Form ES2 of Ensifentrine ethane-1,2-disulfonate according to claim 1, which is characterized by an XRPD pattern having peaks at 14.4, 19.0, 19.7, 26.1 and 31.1 degrees 2-theta±0.2 degrees 2-theta, and also having one, two, three, or four additional peaks selected from 10.4, 17.2, 21.6 and 29.4 degrees two theta±0.2 degrees 2-theta.

3. Crystalline Form ES2 of Ensifentrine ethane-1,2-disulfonate according to claim 1, which is characterized by an XRPD pattern having peaks at: 10.4, 14.4, 17.2, 19.0, 19.7, 21.6, 26.1, 29.4 and 31.1 degrees 2-theta #0.2 degrees 2-theta.

4. Crystalline Form ES2 of Ensifentrine ethane-1,2-disulfonate according to claim 1, which is characterized by: an XRPD pattern substantially as depicted in FIG. 2, and/or a solid state 13C NMR spectrum substantially as depicted in any of FIG. 5*a*, 5*b* or 5*c*.

5. Crystalline Form ES2 of Ensifentrine ethane-1,2-disulfonate according to claim 1, wherein said crystalline form is hydrate form, optionally wherein the crystalline form contains about 5.0% to about 6.0% (w/w) of water.

6. Crystalline Form ES2 of Ensifentrine ethane-1,2-disulfonate according to claim 1, which contains no more than about 20% of any other crystalline forms of Ensifentrine ethane-1,2-disulfonate.

7. Crystalline Form ES2 of Ensifentrine ethane-1,2-disulfonate according to claim 1, which contains no more than about 20% of amorphous Ensifentrine ethane-1,2-disulfonate.

8. A pharmaceutical composition comprising a crystalline form ES2 of Ensifentrine ethane-1,2-disulfonate according to claim 1.

9. A pharmaceutical formulation comprising a crystalline Form ES2 of Ensifentrine ethane-1,2-disulfonate according to claim 1, or a with at least one pharmaceutically acceptable excipient.

10. A process for preparing a pharmaceutical formulation comprising combining a crystalline Form ES2 of Ensifentrine ethane-1,2-disulfonate according to claim 1, with at least one pharmaceutically acceptable excipient.

11. A method of treating chronic obstructive pulmonary disease, cystic fibrosis or asthma, comprising administering a therapeutically effective amount of a crystalline Form ES2 of Ensifentrine ethane-1,2-disulfonate according to claim 1 to a subject in need of the treatment.

12. A medicament for treating chronic obstructive pulmonary disease (COPD), cystic fibrosis and asthma, comprising the crystalline Form ES2 of Ensifentrine ethane-1,2-disulfonate, according to claim 1.

* * * * *